(12) United States Patent
Petersson et al.

(10) Patent No.: US 6,671,527 B2
(45) Date of Patent: Dec. 30, 2003

(54) OPTICAL SENSOR FOR IN SITU MEASUREMENT OF ANALYTES

(75) Inventors: Bo Petersson, Rungsted Kyst (DK); Anders Weber, Skibby (DK)

(73) Assignee: Precisense A/S, Horsholm (DK)

(*) Notice: Subject to any disclaimer, the term of this patent is extended or adjusted under 35 U.S.C. 154(b) by 84 days.

(21) Appl. No.: 09/975,305

(22) Filed: Oct. 12, 2001

(65) Prior Publication Data

US 2002/0058863 A1 May 16, 2002

(30) Foreign Application Priority Data

Oct. 13, 2000 (GB) .............................................. 0025147

(51) Int. Cl.⁷ ................................................ A61B 5/00
(52) U.S. Cl. ........................ 600/316; 600/317; 600/365; 435/14
(58) Field of Search .............................. 600/310, 316, 600/317, 347, 365; 424/1.17, 94.3, 533; 435/4, 14

(56) References Cited

U.S. PATENT DOCUMENTS

| | | | | |
|---|---|---|---|---|
| 4,224,313 A | * | 9/1980 | Zimmermann et al. | 424/1.17 |
| 4,945,050 A | | 7/1990 | Sanford et al. | |
| 5,101,814 A | * | 4/1992 | Palti | 600/347 |
| 5,149,655 A | | 9/1992 | McCabe et al. | |
| 6,040,194 A | * | 3/2000 | Chick et al. | 600/317 |
| 6,163,714 A | | 12/2000 | Stanley et al. | |

FOREIGN PATENT DOCUMENTS

| | | |
|---|---|---|
| WO | WO 94/24263 | 10/1994 |
| WO | WO 97/34652 | 9/1997 |
| WO | WO 98/55869 | 12/1998 |
| WO | WO 99/64580 | 12/1999 |
| WO | WO 00/02048 | 1/2000 |
| WO | WO 00/35530 | 6/2000 |

OTHER PUBLICATIONS

McShane IEEE Trans on BioMed Eng, "Mote Carlo Modeling for Implantable . . . ", Vol 47; No. 5, May 2000.
Ballerstadt and Schultz, Anal Chem 2000, "A Fluorescence Affinity Hollow Fiber Sensor . . . ", Vol 72; No. 17, 4185–4192, Sep. 2000.
Lakowicz and Maliwal, Analytica Chimica Acta, 271, "Optical sensing of glucose . . . ", pp. 155–164, 1993.
Ballerstadt and Schultz, Analytical Chemica Acta, 345, "Competitive–binding assay method based on fluorescence . . . ", pp. 203–212, 1997.
Ryan Russell et al, Analytical Chemistry, vol. 71, No. 15, 3126–3132 "A fluorescence–Based Glucose . . . ".
Wilkins et al Med. Eng. Phys. (1996) 18: 273–288 Glucose Monitoring: state of the art and future . . . .
Atanasov et al Med. Eng. Phys. vol. 18 (1996) No. 8 pp 632–640 Short–term canine implantation etc.
Meadows et al Anal. Chimica Acta 280 (1993) 21–30 Design, manufacture and characterization of an optical . . . .

(List continued on next page.)

*Primary Examiner*—Eric F. Winakur
*Assistant Examiner*—David J. McCrosky
(74) *Attorney, Agent, or Firm*—Nixon & Vanderhye P.C.

(57) ABSTRACT

An assay implantation apparatus is provided comprising a sensor for use for the in vivo measurement of an analyte and means for implanting said sensor within an upper layer of the skin from which it is naturally ejected over time by growth of the skin and progressive replacement of the outer layer of the skin.

The sensor may comprise microparticles containing a chemical assay system into which an analyte may diffuse from intercellular fluid and which assay system can be interrogated remotely by a light signal and a fluorescence sensor.

17 Claims, 3 Drawing Sheets

OTHER PUBLICATIONS

Mansouri et al Biotec 1984 pp 885–890 A Miniature Optical Glucose Sensor Based on Affinity Binding . . . .

Jaremko et al Diabetes Care. vol. 21, No. 3 (1998) pp 444–450 Advances Toward the Implantable . . . .

Jackson Drug. Metab. Dispos. (1981) vol. 9, No. 6, pp 535 540 Intramuscular Absorption and Regional Lymphatic . . . .

Immunoassay Handbook (1994) ed. David Wild Macmillan Press.

Tyagi et al Nature Biology (1998) vol. 16 Multicolor molecular Beacons for allele discrimiation.

* cited by examiner

OPTICAL SENSOR FOR IN SITU MEASUREMENT OF ANALYTES

BACKGROUND OF THE INVENTION

The present invention relates to a sensor for use in the measurement or monitoring of analytes in cutaneous fluid using optical techniques and to an analyte monitoring system using this sensor. The sensor is particularly suitable for use in situations in which analyte levels must be closely monitored, for example with drugs that must be maintained within a narrow therapeutic window or where analyte measurements must be taken repeatedly, such as in diabetes management.

In the management of diabetes, the regular measurement of glucose in the blood is essential in order to ensure correct insulin dosing. Furthermore, it has been demonstrated that in the long term care of the diabetic patient better control the blood glucose levels can delay, if not prevent, the onset of retinopathy, circulatory problems and other degenerative diseases often associated with diabetes. Thus there is a need for reliable and accurate self-monitoring of blood glucose levels by diabetic patients.

Currently, blood glucose is monitored by diabetic patients with the use of commercially available colorimetric test strips or electrochemical biosensors (e.g. enzyme electrodes), both of which require the regular use of a lancet-type instrument to withdraw a suitable amount of blood each time a measurement is made. On average, the majority of diabetic patients would use such instruments to take a measurement of blood glucose twice a day. However, the US National Institutes of Health recently recommended that blood glucose testing should be carried out at least four times a day, a recommendation that has been endorsed by the American Diabetes Association. This increase in the frequency of blood glucose testing imposes a considerable burden on the diabetic patient, both in terms of financial cost and in terms of pain and discomfort, particularly in the long-term diabetic who has to make regular use of a lancet to draw blood from the fingertips. Thus, there is clearly a need for a better long-term glucose monitoring system that does not involve drawing blood from the patient.

There have been a number of recent proposals for glucose measurement techniques that do not require blood to be withdrawn from the patient. Various attempts have been made to construct devices in which an enzyme electrode biosensor is placed on the end of a needle or catheter which is inserted into a blood vessel (Wilkins, E and Atanasov, P, Med. Eng. Phys (1996) 18: 273–288). Whilst the sensing device itself is located within a blood vessel, the needle or catheter retains connection to the external environment. In practice, such devices are not suitable for use in human patients first because the insertion of a needle or catheter into a blood vessel poses an infection risk and is also uncomfortable for the patient and hence not suitable for continuous use. Secondly, devices of this type have not gained approval for use in patients because it has been suggested that the device itself, on the end of a needle or catheter, may be responsible for the shedding of thromboses into the patient's circulation. This obviously poses a very serious risk to the patient's health.

Mansouri and Schultz (Biotechnology 1984), Meadows and Schultz (Anal. Chim. Acta. (1993) 280: pp21–30) and U.S. Pat. No. 4,344,438 all describe devices for the in situ monitoring of low molecular weight compounds in the blood by optical means. These devices are designed to be inserted into a blood vessel or placed subcutaneously but require fibre-optic connection to an external light source and an external detector. Again the location of these devices in a blood vessel carries an associated risk of promoting thromboses and in addition, in one embodiment the need to retain a fibre-optic connection to the external environment is impractical for long-term use and carries a risk of infection.

In the search for a less invasive glucose monitoring technique some attention has also been focussed on the use of infra-red spectroscopy to directly measure blood glucose concentration in blood vessels in tissues such as the ear lobe or finger tip which are relatively "light transparent" and have blood vessels sited close to the surface of the skin (Jaremko, J. and Rorstad, O. Diabetes Care 1998 21: 444–450 and Fogt, E. J. Clin. Chem. (1990) 36: 1573–80). This approach is obviously minimally invasive, but has proven to be of little practical value due to the fact that the infra-red spectrum of glucose in blood is so similar to that of the surrounding tissue that in practical terms it is virtually impossible to resolve the two spectra.

It has been observed that the concentration of analytes in subcutaneous fluid correlates with the concentration of said analytes in the blood, consequently there have been several reports of the use of glucose monitoring devices which are sited in a subcutaneous location. In particular, Atanasov et al. (Med. Eng. Phys. (1996) 18: pp632–640) describe the use of an implantable glucose sensing device (dimensions 5.0× 7.0×1.5 cm) to monitor glucose in the subcutaneous fluid of a dog. The device consists of an amperometric glucose sensor, a miniature potentiostat, an FM signal transmitter and a power supply and can be interrogated remotely, via antenna and receiver linked to a computer-based data acquisition system, with no need for a connection to the external environment. However, the large dimensions of this device would obviously make it impractical for use in a human patient.

Ryan J. Russell et al, Analytical Chemistry, Vol. 71, Number 15, 3126–3132 describes an implantable hydrogel based on polyethyleneglycol containing fluorescein isothiocyanate dextran (FITC-dextran) and tetramethylrhodamine isochiocyanate concavalin A chemically conjugated to the hydrogel network for dermal implantation. The implanted hydrogel spheres are to be transdermally interrogated.

R. Ballerstadt et al, Analytica Chemica Acta, 345 (1997), 203–212 discloses an assay system in which two polymer (dextran) molecules are respectively labelled with first and second fluorophores and are bound together by multivalent lectin molecules, producing quenching. Glucose saturates the binding sites of the lectin, causing disassociation of the two polymers, giving an increase in fluorescence.

Joseph R. Lakowicz et al, Analytica Chimica Acta, 271, (1993), 155–164 describes the use of phase modulation fluorimetry. This substitutes a fluorescence liftime based measurement for the fluorescence intensity based measurements taught in the earlier described art.

Fluorescence lifetime can be measured by a phase modulation technique by exciting fluorescence using light which is intensity modulated at 1 to 200 MHz and measuring the phase shift of the emission relative to the incident light and the modulation of the emission.

In WO91/09312 a subcutaneous method and device is described that employs an affinity assay for glucose that is interrogated remotely by optical means. In WO97/19188 a further example of an implantable assay system for glucose is described which produces an optical signal that can be read remotely. The devices described in WO91/09312 and WO97/19188 will persist in the body for extended periods after the assay chemistry has failed to operate correctly and this is a major disadvantage for chronic applications. Removal of the devices will require a surgical procedure.

WO00/02048 deals with this problem by using a biodegradable material to contain the assay reagents. This however requires careful design of the biodegradable containment systems to obtain optimum results.

There remains a clear need for sensitive and accurate blood glucose monitoring techniques which do not require the regular withdrawal of blood from the patient, which do not carry a risk of infection or discomfort and which do not suffer from the practical disadvantages of the previously described implantable devices.

BRIEF SUMMARY OF THE INVENTION

Accordingly, in a first aspect the present invention provides an assay implantation apparatus comprising a sensor for the in vivo measurement of an analyte and means for implanting said sensor within an upper layer of the skin from which it is naturally ejected over time by growth of the skin and progressive replacement of the outer layer of the skin.

DETAILED DESCRIPTION OF PREFERRED EMBODIMENTS

In accordance with the invention, the sensor is injected to lie within the thickness of the skin sufficiently near to the surface that over a period of time the sensor will approach the surf ace and eventually be lost. The skin comprises several distinct layers. The stratum corneum is a layer of dead cells which is approximately 10 to 25 µm thick. Beneath this is the epidermis. The cells at the top of the epidermis progressively die and form the base of the stratum corneum. New cells are added to the bottom of the epidermis. The upper cells of the stratum corneum are continuously worn away. Thus a particle implanted in the epidermis (like its neighbouring epidermal cells) will gradually rise through the thickness of the epidermis until it comes into the stratum corneum and is eventually shed. Particles injected through the epidermis into the dermis on the other hand will be retained permanently, as in a conventional tattoo. Implantation of the sensor in the present invention wholly within the epidermis will prevent spent sensor material persisting in the body. The thickness of the epidermis varies over the body. It may be as little as 50 µm on the eyelids and as much as 800 µm on the palms of the hands or the soles of the feet.

The implanting means may be adapted to implant the sensor at a depth of less than 200 µm, more preferably not more than 100 µm, most preferably not more than 50 µm.

Particles may be injected into the epidermis by the use of a short hypodermic needle, e.g. one having a needle length appropriate to the implant action depths just given.

For this purpose one may preferably emply a microneedle array as described in WO-A-99/64580. Such arrays may be micro machined from silicon by an etching process such as reactive ion etching to produce for instance a 10 mm square array of 400 1 µm diameter needles. These may be loaded on their exterior with the required sensor particles or materials or may be provided with individual bores for the interior passage of a suspension of the sensor particles or the sensor materials. Instead of conventional through bores the microneedles may have the property of porosity to allow injection therethrough of sensor materials.

Alternatively, particles may be projected into the skin by so called "needleless syringes" which use various methods to impart sufficient velocity to microparticles that they penetrate the stratum corneum. WO94/24263 describes such devices in which gas pressure is accumulated behind a membrane which ruptures to provide an explosive release of gas into which particles are entrained for injection. An explosive device for this purpose is described in U.S. Pat. No. 4,945,050. An electric discharge based device is described in U.S. Pat. No. 5,149,655.

Combined with sensor particles, any of these known cutaneous injection systems may be used in the present invention.

The sensor of the invention incorporates assay means for detecting an analyte or for measuring the amount of an analyte, the readout of the assay being an optical signal. Because the sensor is located within the skin, an optical signal generated in the sensor can be detected transcutaneously (i.e. through the higher layer(s) of the skin) thus obviating the need for any direct connection between the sensor and the external environment. Once the sensor is in place in a cutaneous location analyte measurements can be taken as often as is necessary with no adverse effects. This is a particular advantage in relation to the long-term care of diabetic patients because if glucose measurements are taken more frequently, tighter control can be maintained over the level of glucose in the blood and the risk of developing conditions related to poorly regulated blood glucose, such as retinopathy, arthritis and poor circulation, will be reduced.

Because the sensor of the invention does not itself contain any of the optical components required to interrogate the readout of the assay (these being provided separately and located outside the body) the sensor can easily be provided in a form which is injectable with minimal discomfort to the patient. In a preferred embodiment the components of the assay are incorporated into a matrix material which is permeable to cutaneous fluid thereby allowing analytes such as glucose to enter the sensor by diffusion and to interact with the components of the assay. The matrix material may be an injectable formulation that forms a gel at the point of injection within the skin of the patient. Alternatively, the sensor may be formed from a solid polymeric matrix material incorporating the components of the assay which is again injected cutaneously, the polymeric material typically being of a size suitable for injection through a narrow gauge needle to minimise the discomfort to the patient. When placed epidermally the solid polymeric material absorbs water and expands to form a gel thus hydrating the components of the assay.

The device of the present invention may be biodegradable or hydrolysable in vivo but this is not necessary as natural growth and replacement processes in the skin will lead to the epidermis in which the sensor is implanted being shed so that the sensor is eventually shed with it. Once the sensor has ceased to be functionally effective in the monitoring of analytes a fresh sensor can be simply injected or implanted and there is no need for the old sensor to be surgically removed.

Materials suitable for the construction of such a sensor include biodegradable block copolymers such as those described by Jeong et al., Nature 388: pp 860–862 Aqueous solutions of these materials are thermosensitive, exhibiting temperature-dependent reversible gel-sol transitions. The polymer material can be loaded with the components of the assay at an elevated temperature where the material forms a sol. In this form the material is injectable and on cutaneous injection and subsequent rapid cooling the body temperature and material forms a gel matrix. The components of the assay are suspended within this gel matrix which thus constitutes a sensor suitable for detecting or measuring analytes in cutaneous fluid. Low molecular weight analytes, such as glucose, can freely diffuse into the gel matrix from the surrounding cutaneous fluid. Cutaneous injection of the sol phase material causes neither significant pain or tissue damage.

As an alternative to the gel based sensor described above the sensor may be constructed from a solid or gel-like biodegradable polymer matrix material within which the assay components are distributed. When injected or implanted cutaneously this solid polymer sensor hydrates, swells and analyte penetrates through the structure to encounter the assay components.

Both the solid polymer sensors and the hollow chamber sensors may be introduced into a cutaneous location by injection as described below.

Biodegradable materials suitable for use in the construction of the hollow chamber and solid polymer sensors include cross-linked proteins such as human albumin, fibrin gels, polysaccharides such as starch or agarose, poly (DL-lactide) and poly (DL-glycolide), polyanhydrides, fatty acid/cholesterol mixtures that form semi-solid derivates, hyaluronates and liquid crystals of monooliein and water. Non-biodegradable materials may also be used.

In a still further embodiment, the sensor may be formed as a suspension of microparticles of preferred diameter <100 $\mu$m, more preferably 10 to 100 $\mu$m, e.g. 10 to 50 $\mu$m. However, the particles may be smaller than 10 $\mu$m. Each of the particles may contain the assay components either encapsulated inside a hollow microparticle, or dispersed within the material of a solid microparticle. Such a suspension of microparticles is readily injected cutaneously. Optionally, the microparticles are formed from a material which is biodegradable or hydrolysable in vivo. Alternatively, liposomes containing the assay components can be used. Liposomes of diameter 0.3 to 2.0 $\mu$m have been shown to remain at the site of injection (Jackson A. J., Drug Metab. Dispos. 1981 9, 535–540) so they would be suitable for use in the sensor. In a further embodiment the sensor comprises a plurality of empty erythrocytes which have been loaded with assay components and then injected epidermally. Empty erythrocytes, also known as erythrocyte ghosts, can be prepared by exposing intact erythrocytes to a hypotonic solution so that they swell and burst to release their cytoplasmic contents. The empty erythrocytes can then be loaded with assay components before allowing the plasma membranes to reseal.

In the preferred embodiments of the sensor (i.e. gel, solid polymer, hollow or solid microparticles) it is advantageous for the assay components to have a restricted diffusion in order to minimise their loss from the sensor. This can be achieved by ensuring that the gel or the containment material has a pore size that permits the diffusion of low molecular weight analytes but not the assay components themselves. These would only be lost as the material or gel degrades over time. The assay components are preferably of high molecular weight, such as proteins or polymers, in order to restrict their loss from the sensor.

Assays suitable for use in the sensor include reactions such as hydrolysis and oxidation leading to detectable optical change i.e. fluorescence enhancement or quenching which can be observed transcutaneously. A preferred assay for use in the sensor of the invention is a binding assay, the readout of which is a detectable or measurable optical signal which can be interrogated transcutaneously using optical means. The binding assay generating the optical signal should preferably be reversible such that a continuous monitoring of fluctuating levels of the analyte can be achieved. This reversibility is a particular advantage of the use of a binding assay format in which the components of the assay are not consumed. Binding assays are also preferred for use in the sensor of the invention for reasons of safety as they cannot generate any unwanted products as might be generated by an enzymatic or electrochemical reaction.

Preferred binding assay configurations for use in the sensor of the invention include a reversible competitive, reagent limited, binding assay, the components of which include an analyte analog and an analyte binding agent capable of reversibly binding both the analyte of interest and the analyte analog. The analyte of interest and the analyte analog compete for binding to the same binding site on the analyte binding agent. Such competitive binding assay configurations are well known in the art of clinical diagnostics and are described, by way of example, in The Immunoassay Handbook, ed. David Wild, Macmillan Press 1994. Suitable analyte binding agents for use in the assay would include antibodies or antibody fragments which retain an analyte binding site (e.g. Fab fragments), lectins (e.g. concanavalin A), hormone receptors, drug receptors, aptamers and molecularly-imprinted polymers. Preferably the analyte analog should be a substance of higher molecular weight than the analyte such that it cannot freely diffuse out of the sensor. For example, an assay for glucose might employ a high molecular weight glucose polymer such as dextran as the analyte analog.

Suitable optical signals which can be used as an assay readout in accordance with the invention include any optical signal which can be generated by a proximity assay, such as those generated by fluorescence resonance energy transfer, fluorescence polarisation, fluorescence quenching, phosphorescence technique, luminescence enhancement, luminescence quenching, diffraction or plasmon resonance, all of which are known per se in the art.

The most preferred embodiment of the sensor of the invention incorporates a competitive, reagent limited binding assay which generates an optical readout using the technique of fluorescence resonance energy transfer. In this assay format the analyte analog is labelled with a first chromophore and the analyte binding agent is labelled with a second chromophore. One of the first and second chromophores acts as a donor chromophore and the other acts as an acceptor chromophore. It is an essential feature of the assay that the fluorescence emission spectrum of the donor chromophore overlaps with the absorption spectrum of the acceptor chromophore, such that when the donor and acceptor chromophores are brought into close proximity by the binding agent a proportion of the energy which normally would produce fluorescence emitted by the donor chromophore (following irradiation with incident radiation of a wavelength absorbed by the donor chromophore) will be non radiatively transferred to the adjacent acceptor chromophore, a process known in the art as fluorescence resonance energy transfer, with the result that a proportion of the fluorescent signal emitted by the donor chromophore is quenched and, in some instances, that the acceptor chromophore emits fluorescence. Fluorescence resonance energy transfer will only occur when the donor and acceptor chromophores are brought into close proximity by the binding of analyte analog to analyte binding agent. Thus, in the presence of analyte, which competes with the analyte analog for binding to the analyte binding agent, the amount of quenching is reduced (resulting in a measurable increase in the intensity of the fluorescent signal emitted by the donor chromophore or a fall in the intensity of the signal emitted by the acceptor chromophore) as labelled analyte analog is displaced from binding to the analyte binding agent. The intensity or lifetime of the fluorescent signal emitted from the donor chromophore thus correlates with the concentration of analyte in the subcutaneous fluid bathing the sensor.

An additional advantageous feature of the fluorescence resonance energy transfer assay format arises from the fact that any fluorescent signal emitted by the acceptor chromophore following excitation with a beam of incident radiation at a wavelength within the absorption spectrum of the acceptor chromophore is unaffected by the fluorescence resonance energy transfer process. It is therefore possible to use the intensity of the fluorescent signal emitted by the acceptor chromophore as an internal reference signal, for example in continuous calibration of the sensor or to monitor the extent to which the sensor has degraded and thus indicate the need to implant or inject a fresh sensor. As the sensor degrades, the amount of acceptor chromophore present in the sensor will decrease and hence the intensity of fluorescent signal detected upon excitation of the acceptor chromophore will also decrease. The fall of this signal below an acceptable baseline level would indicate the need to implant or inject a fresh sensor. Competitive binding assays using the fluorescence resonance energy transfer technique which are capable of being adapted for use in the sensor of the invention are known in the art. U.S. Pat. No. 3,996,345 describes immunoassays employing antibodies and fluorescence resonance energy transfer between a fluorescer-quencher chromophoric pair. Meadows and Schultz (Anal. Chim. Acta (1993 280: pp21–30) describe a homogeneous assay method for the measurement of glucose based on fluorescence resonance energy transfer between a labelled glucose analog (FITC labelled dextran) and a labelled glucose binding agent (rhodamine labelled concanavalin A). In all of these configurations the acceptor and donor chromophores/quenchers can be linked to either the binding agent or the analyte analog.

The various FRET chemistries described in the background art cited in the introduction of this document may be used.

Fluorescence lifetime or fluorescence intensity measurements may be made. As described in Lakowitz et al, fluorescence lifetime may be measured by phase modulation techniques.

An alternative to the fluorescence resonance energy transfer is the fluorescence quenching technique. In this case a compound with fluorescence quenching capability is used instead of the specific acceptor chromophore and the optical signal in a competitive binding assay will increase with increasing analyte. An example of a powerful and non-specific fluorescence quencher is given by Tyagi et al. Nature Biotechnology (1998) 18: p49.

The sensor of the invention can be adapted for the detection or quantitative measurement of any analyte present in subcutaneous fluid. Preferred analytes include glucose (in connection with the long-term monitoring of diabetics), urea (in connection with kidney disease or dysfunction), lactate (in connection with assessment of muscle performance in sports medicine), ions such as sodium, calcium or potassium and therapeutic drugs whose concentration in the blood must be closely monitored, such as, for example, digoxin, theophylline or immunosuppressant drugs. The above analytes are listed by way of example only and it is to be understood that the precise nature of the analyte to be measured is not material to the invention.

The sensor is interrogated transcutaneously using optical means i.e. no physical connection is required between the sensor and the optical means. When the sensor incorporates a competitive, reagent limited, binding assay employing the technique of fluorescent energy transfer, the optical means should supply a first beam of incident radiation at a wavelength within the absorption spectrum of the donor chromophore and preferably a second beam of incident radiation at a wavelength within the adsorption spectrum of the acceptor chromophore. In addition, the optical means should be capable of measuring optical signals generated in the sensor at two different wavelengths; wavelength 1 within the emission spectrum of the donor chromophore (the signal generated in connection with the measurement of analyte and wavelength 2 in the emission spectrum of the acceptor chromophore (which could be the analyte signal or the internal reference or calibration signal).

Optical means suitable for use in remote interrogation of the device of the invention include a simple high-throughput fluorimeter comprising an excitation light source such as, for example, a light-emitting diode (blue, green or red>1000 mCa), an excitation light filter (dichroic or dye filter) and a fluorescent light detector (PIN diode configuration). A fluorimeter with these characteristics may exhibit a sensitivity of between picomolar to femtomolar fluorophore concentration.

A suitable fluorimeter set-up is shown in the accompanying FIG. 1 and described in the Examples included herein. The fluorimeter separately measures the following parameters:

At wavelength 1 (donor chromophore)
Excitation light intensity, $I(1,0)$
Ambient light intensity, $I(1,1)$
Intensity of combined fluorescent and ambient light, $I(1,2)$ At wavelength 2 (acceptor chromophore)
Excitation light intensity, $I(2,0)$
Ambient light intensity, $I(2,1)$
Intensity of combined fluorescent and ambient light, $I(2,2)$ Measurements are taken by holding the fluorimeter close to the skin and in alignment with the sensor. When making transcutaneous measurements of the fluorescent signals generated in the sensor it is necessary to take account of the absorption of signal by the skin, the absorptivity of human skin is found by experiment to be lowest in the range from 400 nm to 900 nm. The final output provided is the normalised ratio between the fluorescent intensity from the two fluorophores, defined by the following relation (Equation 1):

$$\text{Final output} = (I(1,2)-I(1,1))*I(2,0)/(I(2,2)-I(2,1))*I(1,0) \tag{1}$$

In a fourth aspect the invention provides a method of detecting or quantitatively measuring an analyte in the cutaneous fluid of a mammal, which method comprises the steps of,
(a) injecting or implanting a sensor for the detection or quantitative measurement of an analyte in the epidermis or within the skin such that it is expelled spontaneously with time;
(b) allowing the assay of said assay to reach thermodynamic equilibrium;
(c) interrogating the readout of said assay using optical means; and (d) relating the measurement obtained in (c) to the concentration of analyte.

The final output from the optical means (e.g. the fluorimeter) as given by Equation 1 above is converted to analyte concentration preferably by means of a computer using calibration data which can be obtained based on the principles set out below.

A calibration curve can be established empirically by measuring response versus analyte concentration for a physiologically relevant range of analyte concentrations. Preferably, this take place in vitro as part of the production of the sensor device. The calibration procedure can be simplified considerably by using the mathematical relation between response and analyte concentration in a competitive affinity sensor which is derived as follows:

The response of a competitive affinity sensor is governed by the reactions:

$$RC \rightleftharpoons R+C$$

$$RL \rightleftharpoons R+L$$

Designating the dissociation of the complexes RC and RL, formed by the combination of analyte binding agent (R) with analyte (L) or analyte analog (C).

The corresponding dissociation equilibrium constants are:

$$K_1 = \frac{C_r C_c}{C_{RC}} \quad \text{and,} \quad K_2 = \frac{C_r C_c}{C_{RL}}$$

where C designates the number of moles of the species in the sensor divided by the sensor volume. Using this measure of concentration both immobilised species and species in solution are treated alike.

The mass balance equations are:

$$T_C = C_C + C_{RC}$$

for total analyte analog concentration and, $$T_R = C_R + C_{RC} + C_{RL}$$

for total analyte binding agent concentration.

Using the expression above, the relation between response and analyte concentration is derived;

$$\frac{T_C - C_C}{C_C} K_1 = \frac{T_R - (T_C - C_C)}{1 + (C_L/K_2)} \quad (2)$$

By using this relation the amount of data necessary for the calibration can be reduced to two key parameters: Total analyte binding agent concentration and total analyte analog concentration. The calibration curve is thus determined by two points on the curve.

BRIEF DESCRIPTION OF THE SEVERAL VIEWS OF THE DRAWINGS

The present invention will be further understood with reference to the following non-limiting examples, together with the accompanying figures in which.

DESCRIPTION OF THE ILLUSTRATED EMBODIMENT

Figure 3:
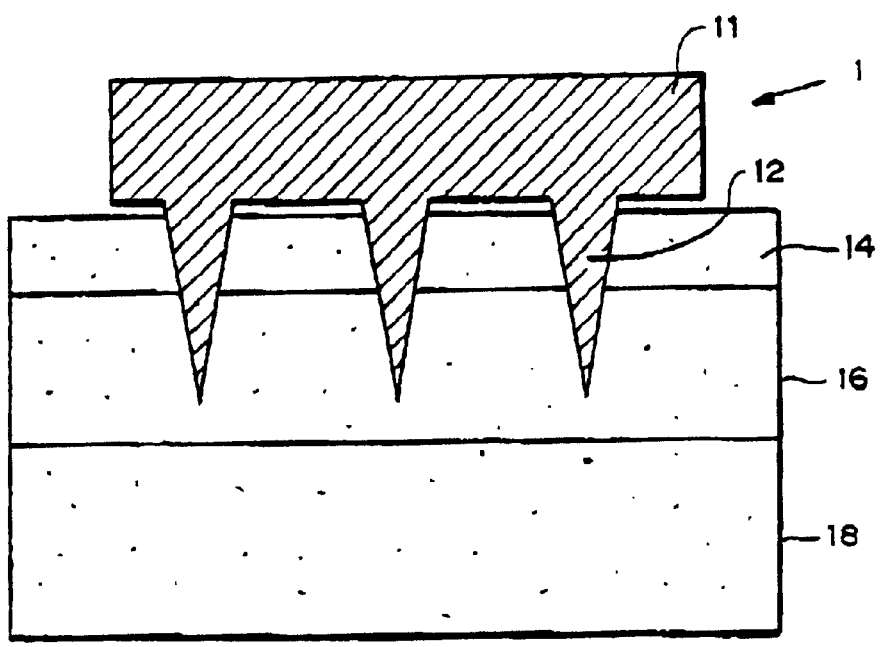
FIG. 3, ken from WO 99/64580, shows a multineedle injector which is suitable for use in the invention, viewed in side elevation.

As seen in FIG. 3, a suitable known form of injector 1 comprises a silicon substrate 11 on one face of which an array of microneedles 12 has been formed over a rectangular area by photolithography and reactive ion etching or a similar process. Suitably, the needles are of between 1 and 800 μm e.g. 50 μm in length and may be solid as shown or hollow with a through bore for the passage of the sensor material.

As schematically shown in FIG. 3, each microneedle is pressed into the skin of a subject, passing through the stratum corneum 14, into the epidermis 16, but stopping short of the dermis 18.

EXAMPLES

Example 1

A glucose assay according to Meadows and Schultz (Talanta, 35, 145–150, 1988) was developed using concanavalin A-rhodamine and dextran-FITC (both from Molecular Probes Inc., Oregan, USA) The principle of the assay is fluorescence resonance energy transfer between the two fluorophores when they are in close proximity; in the presence of glucose the resonance energy transfer is inhibited and the fluorescent signal from FITC (fluorescein) increases. Thus increasing fluorescence correlates with increasing glucose. The glucose assay was found to respond to glucose, as reported by Schultz, with approximately 50 percent recovery of the fluorescein fluorescence signal at 20 mg/dL glucose. Fluorescence was measured in a Perkin Elmer fluorimeter, adapted for flow-through measurement using a sipping device.

Example 2

The glucose assay components of Example 1 were added so stirred solutions (1 ml) of 1%, 1.5% and 2% w/v of a low melting temperature agarose (Type IX, Sigma, St. Louis, USA) at 45° C. After dispersal, the temperature was reduced to 20° C. and the stirring was stopped. When the gel had formed (after approximately 3 hours) it was placed in a ceramic mortar and ground to a particle size of 50 to 100 μm, by visual reference to a polystyrene bead preparation with the same mean bead diameter. The particle preparation was suspended in 0.9% w/v saline and filtered through a nylon mesh to remove the larger particles. The particles that passed through the mesh were then centrifuged in a bench centrifuge at 500 g and the supernatant containing tines was discarded. During the process the particles retained their fluorescence by visual inspection and by measurement of the rhodamine fluorescence in the Perkin Elmer fluorimeter. Adding glucose at 20 mg/dL to a sample of the suspended particles resulted in a rise in the fluorescein fluorescence signal over a 30 minute period. Thus the assay components contained with the agarose gel were responsive to glucose.

Example 3

Figure 1:
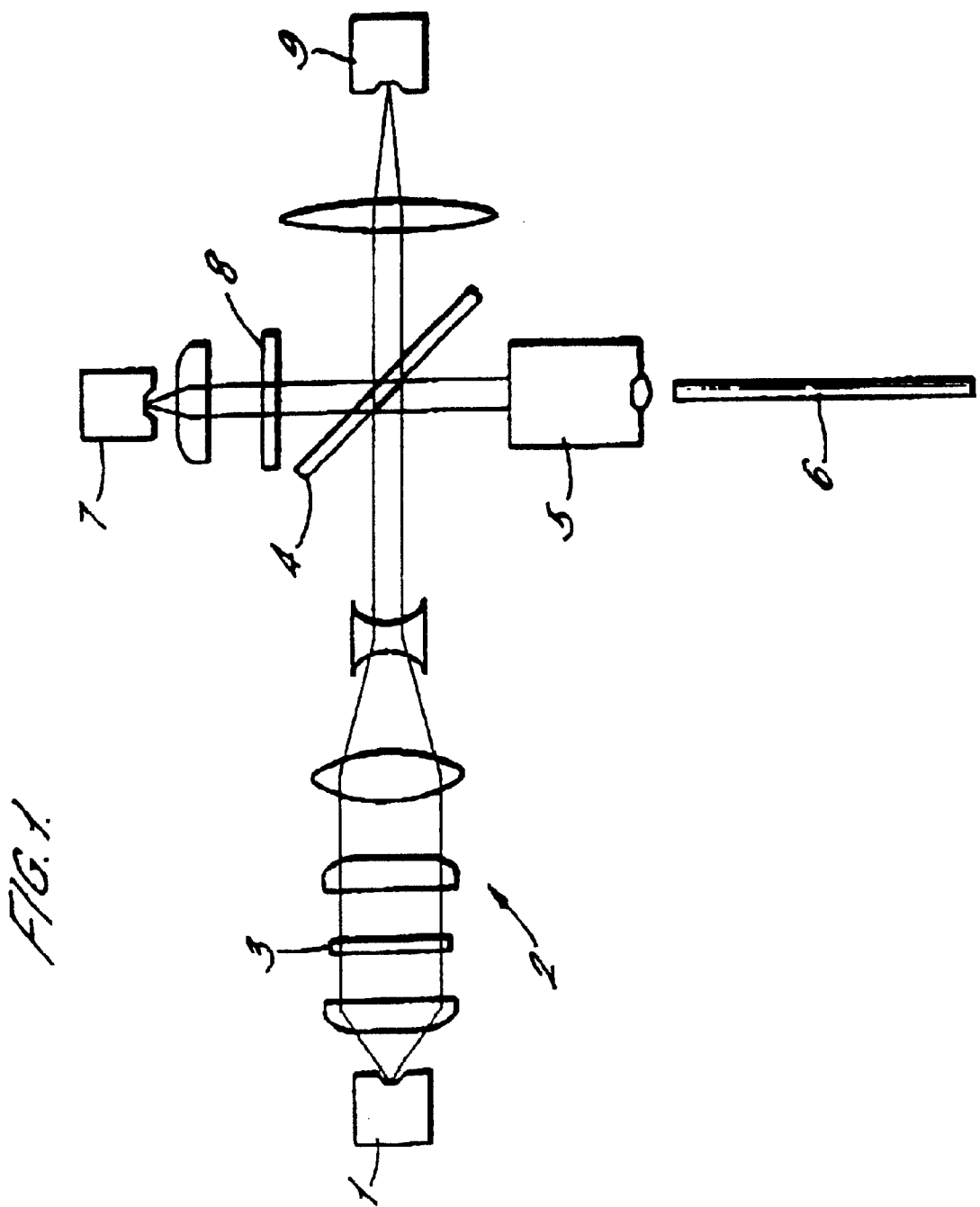
FIG. 1 is a schematic diagram of the optical part of the fibre optic fluorimeter.
Figure 2:
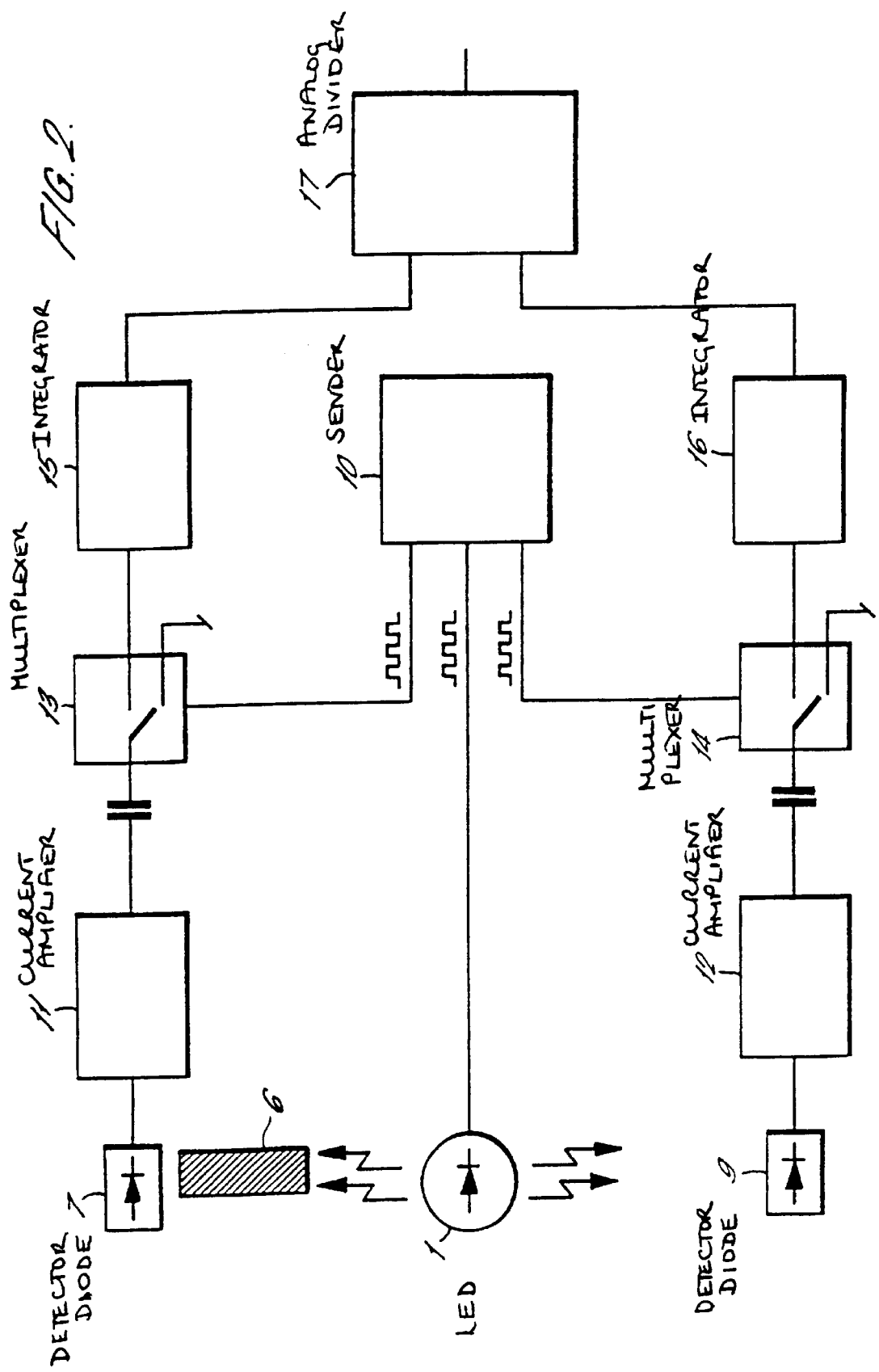
FIG. 2 is a schematic diagram of a driver/amplifier circuit used in conjunction with the optical part of the fibre optic fluorimeter.

A fibre optic fluorimeter was assembled as follows:

The optical part of a fibre optic fluorimeter was made from standard components on a micro bench. The set-up, comprising a red LED as light source, lenses, dichroic beamsplitter and filters and detector diodes, was as shown in FIG. 1. Briefly, the fluorimeter comprises a light emitting diode (1) providing an excitation light beam which passes through a condenser (2) containing an excitation filer (3) and is incident upon a beamsplitter (4). Part of the excitatory beam is thereby deflected into launching optics (5) and enters an optical fibre (6). When the fluorimeter is in use in the interrogation of a cutaneously located sensor the end of the skin, in alignment with the cutaneous sensor, so that beam of excitatory light is incident upon the sensor a portion of the optical signal emitted from the sensor following excitation enters the optical fibre (6) and is thereby conveyed into the fluorimeter where it passes through a blocking diode (7). The fluorimeter also contains a reference detector diode (9) which provides a reference measurement of the excitatory light emitted from the LED (1). The ends of a 1 m long Ensign Beckford optical fibre, 0.5 mm in diameter, numerical aperture of 0.65, were ground to a mirror finish using diamond paste on glass paste. One end of the fibre was mounted in an X Y Z holder in front of a 20× microscope objective. The diodes (LED (1) and detector diodes (7) and (9)) were connected to a custom made driver/amplifier circuit as shown in FIG. 2. The circuit comprises a sender (10), current amplifiers (11) and (12), multiplexers (13) and (14), integrators (15) and (16) and analog divider (17). The driver circuit was set to drive the LED (1) at 238 Hz and the signals from the detector diodes (7) and (9) were switched between ground and the storage capacitors (integrator with a time constant of 1 second) synchronised with the drive signal. The two integrated signals correspond to background-corrected fluorescent signal and background corrected excitation light level (LED intensity). The former divided by the latter was supported by an analog divider as shown in FIG. 2. For test purposes, the distal end of the fibre (6) was dipped into dilute solutions of rhodamine and the optics were adjusted for maximum signal from the analog divider.

The fluorimeter is battery operated (typical power consumption 150 mA at 9V) and for convenience can be constructed in the shape and dimensions of a pen.

Example 4

1.5% w/v agarose particles of approximately 50 µm diameter containing the assay components (as described in Example 2) are washed several times by centrifuging and resuspending in 0.9% w/v saline solution. This washing procedure removes excess reagents that were not trapped within the gel structure. The particles remain highly fluorescent during this process. Then the particle suspension is loaded on to a silicon micromachined pad having a 10 mm square array of 400 microneedles of 1 µm diameter having a penetration depth from the skin surface of 100 µm and injected cutaneously or intradermally under the skin on the back of the hand of a human volunteer. A fibre optic fluorimeter (see Example 3) is directed at the skin and a rhodamine fluorescence signal is obtained and correlated with a conventional blood glucose measurement indicating that transdermal measurements can be made on implanted sensors. The sensor particles are lost from the skin after a period of one month.

We claim:

1. An assay implantation apparatus comprising:
   a sensor for the in vivo measurement of an analyte; and
   means for implanting said sensor within an upper layer of the skin from which the sensor is naturally ejected over time by growth of the skin and progressive replacement of the outer layer of the skin.

2. Apparatus as claimed in claim 1, wherein said implantation means comprises at least one injection needle having a length penetrable into the skin of no more than 200 µm.

3. Apparatus as claimed in claim 1, comprising means for projecting said sensor into the skin to penetrate to the required depth within the skin.

4. Apparatus as claimed in claim 1, wherein said sensor comprises a multitude of micro-particles, each comprising an assay for said analyte, said assay producing a readout upon interrogation which readout is an optical signal which is detectable or measurable transcutaneously by external optical means.

5. Apparatus as claimed in claim 1, wherein said assay is a binding assay, a readout of which is a detectable or measurable optical signal.

6. Apparatus as claimed in claim 5, wherein said binding assay is a competitive binding assay components of which include an analyte binding agent and an analyte analog.

7. Apparatus as claimed in claim 6, wherein said analyte analog is labelled with a first chromophore and said analyte binding agent is labelled with a second chromophore, an emission spectrum of said first chromophore overlapping with an absorption spectrum of said second chromophore.

8. Apparatus as claimed in claim 5 or claim 6, wherein the analyte binding agent is an antibody, an Fab fragment, a lectin, a hormone receptor, a drug receptor, an aptamer or a molecularly-imprinted polymer.

9. Apparatus as claimed in claim 5, wherein said detectable or measurable optical signal is generated by fluorescence resonance energy transfer, fluorescence polarisation, fluorescence quenching, phosphorescence, luminescence enhancement, luminescence quenching, diffraction or plasmon resonance.

10. Apparatus as claimed in claim 1, wherein the sensor comprises a matrix material, the components of said assay being suspended in said matrix material.

11. Apparatus as claimed in claim 1, wherein said sensor comprises solid microparticles and the components of said assay are uniformly dispersed in said solid microparticles.

12. Apparatus as claimed in claim 1, wherein said sensor comprises hollow microparticles and the components of said assay are encapsulated inside said hollow microparticles.

13. Apparatus as claimed in claim 1, wherein said sensor comprises a plurality of liposomes, the components of said assay being encapsulated inside said liposomes.

14. Apparatus as claimed in claim 1, wherein said sensor comprises a plurality of empty erythrocytes which have been loaded with the components of said assay.

15. An analytical system for the detection or quantitative measurement of an analyte in cutaneous fluid, which analytical system comprises, assay implantation apparatus as claimed in claim 1 together with optical means suitable for the transcutaneous interrogation of said sensor.

16. A method for in vivo assay of an analyte comprising:
   placing a sensor within an upper layer of the skin from which the sensor is naturally ejected over time by growth of the skin and progressive replacement of the outer layer of the skin.

17. A method as claimed in claim 16, wherein the sensor is placed below the stratum corneum and within the epidermis.

* * * * *